United States Patent [19]

Takafuji et al.

[11] Patent Number: 4,539,848
[45] Date of Patent: Sep. 10, 1985

[54] METHOD OF DETERMINING GRAIN SIZE USING ULTRASONIC WAVES

[75] Inventors: Hideo Takafuji; Shoichi Sekiguchi, both of Kawasaki, Japan

[73] Assignee: Nippon Steel Corporation, Tokyo, Japan

[21] Appl. No.: 634,478

[22] Filed: Jul. 25, 1984

[30] Foreign Application Priority Data

Aug. 1, 1983 [JP] Japan ................................. 58-139390

[51] Int. Cl.$^3$ ............................................ G01N 29/00
[52] U.S. Cl. ........................................ 73/599; 73/602
[58] Field of Search ................ 73/599, 60 L, 589, 629

[56] References Cited

U.S. PATENT DOCUMENTS 4,026,157 5/1977 Goebbels .............................. 73/599
4,165,649 8/1979 Greer, Jr. ............................ 73/599

FOREIGN PATENT DOCUMENTS 53-126991 11/1978 Japan .

OTHER PUBLICATIONS

Conference Report, "Eighth World Conference on Nondestructive Testing", section 3F, Quantitative Determination of Grain Sizes by means of Scattered Ultrasound, pp. 1-7, Sep. 9, 1976.
R. Klinman et al., "Ultrasonic Prediction of Grain Size, Strength, and Toughness in Plain Carbon Steel," *Materials Evaluation*, pp. 26–32, Oct. 1980.
N. M. Bilgutay et al., "The Effect of Grain Size on Flaw Visibility Enhancement Using Split-Spectrum Processing," *Materials Evaluation*, pp. 808–814, May 1984.

*Primary Examiner*—Stephen A. Kreitman
*Attorney, Agent, or Firm*—Wenderoth, Lind & Ponack

[57] ABSTRACT

The grain size is expressed by the diameter of grains demarcated at high-angle grain boundaries, such as ferrite grains in ferritic steels. Ultrasonic waves having a frequency f are propagated through an object to be examined and its attenuation constant $\alpha$ is determined. Using the ratio $f/\alpha$ and equation $$C'_j \leq f/\alpha \leq C'_{j+1}$$

where $C'_j$ and $C'_{j+1}$ are constants and j is a constant between 1 and 4, the order j of the region to which the value of $f/\alpha$ belongs is determined. Then the grain diameter D is derived from equation $$D = \left( \frac{\alpha}{A_j \cdot f^{n_j+1}} \right)^{\frac{1}{n_j}}$$

using an integer $n_j$ and constant $A_j$ predetermined for the order j of each region.

1 Claim, 10 Drawing Figures

4,539,848

METHOD OF DETERMINING GRAIN SIZE USING ULTRASONIC WAVES

BACKGROUND OF THE INVENTION

1. Field of the Invention

This invention relates to a method of determining grain size by measuring the attenuation of ultrasonic waves.

2. Description of the Prior Art

Examining how ultrasonic waves attenuate within materials offers an effective approach for determining their physical and other properties that are useful from the viewpoint of materials science. Especially, many attempts have been made at establishing relationships between the micro-structural characteristics of materials, such as the grain size of steel, and their attenuation constant of ultrasonic waves. When the steel structure consists of only one phase, ferrite or austenite, their grain size has been considered to be estimated. In reality, however, the steel structure is not limited to ferrite and austenite. There are such highly complex structures as pearlite, martensite, bainite and tempered martensite. Some of them are often even mixed in the same steel. Relationships of these structures with the attenuating characteristics of ultrasonic waves have not been very clear. It has been only vaguely guessed that different structures might have different attenuation constants. No definite relationship has been established between the attenuation constants and grain size.

The inventors already proposed a method of determining grain size using ultrasonic waves (refer to Japanese Patent Provisional Publication No. 126991 of 1988). However, this previous method had several limitations on measuring conditions: attenuation constant of ultrasonic waves $\alpha = 2$ dB/cm or above, discrimination accuracy $= \pm 1.0$ of ASTM grain-size numbers, and steel thickness = approximate 50 mm or under.

SUMMARY OF THE INVENTION

This invention has been made as an improvement over the previous method just mentioned. The object of this invention is to provide a method of determining grain size using ultrasonic waves with a higher degree of accuracy than ever, covering a wider range of ultrasonic-wave attenuation constants and steel thickness.

The grain size as used for this invention is the mean diameter of grains that can be demarcated in the high-angle grain boundaries where crystallographic orientation varies extensively, such as the ferrite grains in ferritic steels.

According to the method of this invention, grain size is determined using ultrasonic waves as follows: Ultrasonic waves having a frequency f are propagated through the object to be examined, and the attenuation constant $\alpha$ of the waves is determined. Then, the order j of the region to which the value of the ratio $f/\alpha$ belongs is determined using the ratio $f/\alpha$ and the following equation $$C'_j \leq f/\alpha \leq C'_{j+1}$$

where $C'_j$, $C'_{j+1}$ = constants, and
j = constant between 1 and 4.

Using integer $n_j$ and constant $A_j$ predetermined for each order j, grain diameter D is derived from the following equation $$D = \left( \frac{\alpha}{A_j \cdot f^{n_j+1}} \right)^{\frac{1}{n_j}}$$

The grain diameter thus determined can be translated into the commonly employed grain size such as ASTM grain-size number.

DESCRIPTION OF THE PREFERRED EMBODIMENTS

A feature of this invention is to put into shape the concept of effective grains discussed later and establish its fundamental relationship with the attenuation of ultrasonic waves. And as such, it is now possible to estimate with high accuracy the grain size, especially the effective grain size that practically governs mechanical properties, of steel on the basis of the attenuation constant of ultrasonic waves determined. This method is applicable not only to ferritic and pearlitic steels but also to martensitic, bainitic and other steels with more complex structures.

Figure 1:
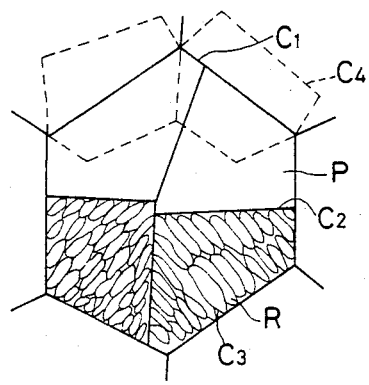
FIG. 1 is a schematic view illustrating martensitic and bainitic structures.

Effective grains are the grains with grain boundaries where crystallographic orientation changes greatly. As is well known, rapid cooling of heated steel usually causes grains to grow finer. FIG. 1 shows the microstructure resulting from the austenite-to-martensite transformation of a grain triggered by cooling. In this figure, the substantially hexagonal curve $C_1$ indicates the old austenite grain boundaries within which were held a group of small-sectioned laths R oriented in the same direction. The group P enclosed by the bold line $C_2$ is called the covariant packet, with the boundary thereof, indicated by the bold line $C_2$, known as the covariant packet boundary. The boundary $C_3$ surrounding the lath R is called the martensite-lath boundary. The martensite-lath is the finest unit of martensite structure, usually having a width of approximately 1 $\mu$m. The length varies with the austenite grain diameter. Crystals at the boundary $C_3$ are oriented in different directions but the angle of directional variation is not greater than 1 degree. Characteristically, this variation is much smaller than that at ordinary grain boundaries. When plain ferritic steel is cooled, ferrite grains having the boundary as indicated by the dotted line $C_4$ appears. These ferrite grains contain no such small sections as the martensite laths R.

While the orientational variation at the martensite-lath boundary $C_3$ is not greater than 1 degree, that at the covariant packet boundary $C_2$ is as great as tens of degrees. The covariant packet boundary $C_2$, like the ferrite grain boundaries in ferritic steels, is a high-angle grain boundary. High-angle grain boundaries prevent or inhibit the growth of cracks initiated in steel and remarkably attenuate the ultrasonic waves propagating through steel. No low-angle grain boundaries has these functions. Given that the grains demarcated by the high-angle grain boundaries, such as the ferrite grain in ferritic steel and covariant packet P in martensitic and bainitic steels, are the effective grain, then close relationship can be established between the grains of steel and its ultrasonic wave attenuating characteristic and mechanical properties.

Figure 2:
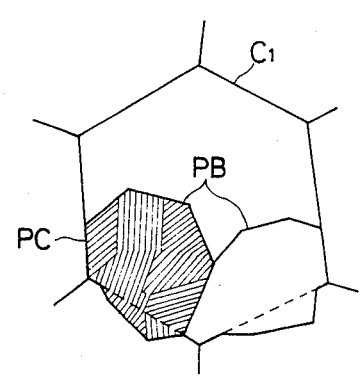
FIG. 2 is a schematic view illustrating pearlitic structure.

In the pearlite structure, the pearlite block PB and pearlite colony PC respectively correspond to the covariant packet and lath boundary of martensite, as shown in FIG. 2. This invention is based on these concepts which are definitely substantiated by the results of measurement referred to later.

Another feature of this invention, which in effect constitutes the most remarkable feature of this grain-size determining method, lies in the fact the grain size as defined before is determined from the attenuation constant of ultrasonic waves.

Grain size is an important parameter affecting the mechanical properties of steel. Studies have been made as to the nondestructive determination of grain size by taking advantage of the relationship between the grain size and the structure of steel and the attenuation of ultrasonic waves passed therethrough. It has been known, for example, that the attenuation constant of ultrasonic waves in the Rayleigh scattering region where the wavelength is sufficiently greater than grain diameter, is proportional to the third power of grain diameter D and the fourth power of the frequency f of ultrasonic waves. This relationship does not hold when the wavelength becomes smaller than the grain diameter D; the attenuation constant $\alpha$ is then proportional to the first power of the grain diameter D and the second power of the frequency f. These relationships can be formulated as follows:

$$\alpha = A_1 D^3 f^4 \quad \lambda/D > C \qquad (1)$$

$$\alpha = A_2 D f^4 \quad \lambda/D < C \qquad (2)$$

The foregoing relationships were derived by empirically determining the attenuation constant $\alpha$ of ultrasonic waves using specimens whose grain diameter D was already known. When determining grain size from the attenuation constant of ultrasonic waves, as intended by this invention, however, grain diameter D is still unknown and, therefore, there is no knowing which of equations (1) and (2) should be employed. A concrete solution to this problem will be described in the following.

With equations (1) and (2), applicable ranges are divided by the value of $\lambda/D$. Actually, however, no such clear-cut separation is possible. The experimental results on which this invention is based made it clear that there is a transitional region where the attenuation constant $\alpha$ is proportional to the second power of the grain diameter and the third power of the frequency of ultrasonic waves. If $\lambda/D$ is adequately large, the attenuation constant $\alpha$ becomes proportional to the second power of the grain diameter D and the third power of the frequency f. By taking into account these facts, equations (1) and (2) can be rewritten into general equation (3).

$$\alpha = A_j D^{nj} f^{nj+1} \qquad C_j \leq \lambda/D \leq C_{j+1} \qquad (3)$$

Assuming that the ultrasonic waves travel through steel at velocity V (cm/sec), then $$\lambda = V/f \qquad (4)$$

From equations (3) and (4), $$\alpha = A_j (D \cdot f)^{nj} \cdot f$$

$$D \cdot f = n_j \sqrt{\frac{1}{A} \frac{\alpha}{f}}$$

$$\lambda/D = \frac{V}{D \cdot f} = V \cdot n_j \sqrt{A_j \frac{f}{\alpha}}$$

Accordingly, equation (3) can be rearranged as $$\alpha = A_j D^{nj} f^{nj+1} \qquad C'_j \leq f/\alpha \leq C'_{j+1} \qquad (5)$$
$$(j = 1, 2, 3, 4)$$

where $$C'_j = \frac{1}{A_j} \left(\frac{C_j}{V}\right)^{nj}$$

$$C'_{j+1} = \frac{1}{A_j} \left(\frac{C_{j+1}}{V}\right)^{nj}$$

Also, j=1, n=1; j=2, n=2; j=3, n=3, and j=4, n=2.

The attenuation constant $\alpha$(dB/cm) can be obtained by determining the attenuation of an appropriate frequency f(c/s). Then, the value of the ratio f/$\alpha$ is determined. With the value of n obtained from equation (5), the grain diameter D is derived from the following equation.

$$D = \left(\frac{\alpha}{A_j \cdot f^{nj+1}}\right)^{\frac{1}{nj}} \qquad (6)$$

Namely, the boundary conditions defining the regions where the relationships among the attenuation constant $\alpha$, grain diameter D and frequency f of ultrasonic waves vary can now be expressed in terms of the attenuation constant α measured rather than the unknown grain diameter D. Therefore, the unknown grain diameter D can now be determined from the measure of the attenuation constant of ultrasonic waves using equation (6).

The following paragraphs describe the concrete method of determining grain diameter according to this invention.

First, the attenuation constant α(dB/cm) of ultrasonic waves was determined using a sample steel whose grain diameter D (mm) was known (the grain size having been previously measured according to the conventional method). Then, the following relationships were empirically established between α and λ/D:

When $\lambda/D \leq 5.5$, $\alpha = 0.52Df^2$
When $5.5 \leq \lambda/D \leq 7.0$, $\alpha = 0.49D^2f^3$
When $7.0 \leq \lambda/D \leq 9.5$, $\alpha = 0.58D^3f^4$
When $\lambda/D \geq 9.5$, $\alpha = 0.36D^2f^3$ When D is unknown, however, the value of λ/D is also unknown; therefore a choice of appropriate equation is impossible. Equation (3), however, can be replaced by another equation in which f/α, rather than λ/D, used as a parameter, as described in the following.

When $f/\alpha \leq 1.79$, $\alpha = 0.52Df^2$
When $1.79 \leq f/\alpha \leq 2.86$, $\alpha = 0.49D^2f^3$
When $2.86 \leq f/\alpha \leq 7.14$, $\alpha = 0.58D^3f^4$
When $f/\alpha \geq 7.14$, $\alpha = 0.36D^2f^3$ As the value of f/α is known, D can be derived from α and f. In these equations, f is the measured frequency (MHz), λ is the ratio V/f (mm), V is the velocity of sound travelling through steel (5900 m/s), and α is the attenuation constant corrected for diffraction and reflection losses.

These above relationships are for the case of longitudinal wave. They are different for the shear wave.

Figure 3:
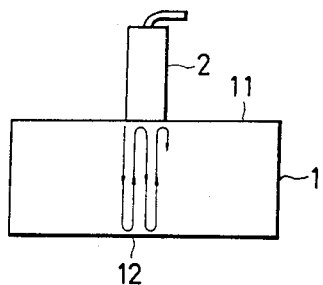
FIG. 3 is a schematic view of a device that determines the attenuation constant of ultrasonic waves.
Figure 4:
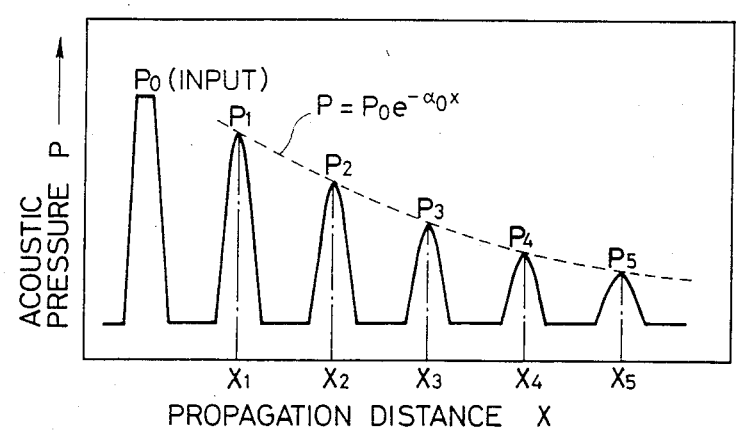
FIG. 4 is a graphical representation of the attenuation constant of ultrasonic waves determined.

In FIG. 3, reference numeral 1 designates the object steel to be examined and item 2 is an ultrasonic generator capable of both transmitting and receiving. Ultrasonic waves produced by the ultrasonic generator 2 kept in contact with the surface 11 of the object 1 propagate through the object 1, being reflected at the bottom surface 12 and re-reflected at the surface 11 and repeating this cycle. The series of acoustic pressures resulting from the multiple reflections of the ultrasonic waves between the surfaces 11 and 12 and detected by the generator 2 forms an attenuation curve as shown in FIG. 4. The acoustic pressure P of the echoes can be expressed as $P = P_o e^{-\alpha x}$, attenuating substantially exponentially with respect to the distance of propagation X (cm) as illustrated in FIG. 4. If the acoustic pressure at propagation distance $X_1$ and $X_2$ (cm) in steel are respectively $P_1$ and $P_2$, then the attenuation constant α(dB/cm) can be expressed as follows:

$$\alpha = \frac{20 \log (P_1/P_2)}{X_2 - X_1}$$

Actually, the attenuation of ultrasonic waves results from not only the scattering at grain boundaries which is dealt with by this invention but also ultrasonic diffraction in steel, reflection losses at both surfaces of steel, and other causes. These parameters, however, are experimentally established as the functions of steel thickness which can be used for correction. As such, the attenuation constant α used in this description is that which has been appropriately corrected and, therefore, can be construed as having been caused solely by grains.

This true attenuation constant α is obtained using a correcting equation shown below that is previously derived based on experimental results.

Diffraction loss: $\Delta \alpha_d = 3.0/f$ (dB/cm)
Reflection loss: $\Delta \alpha_r = 0.25\sqrt{f/2d}$ (dB/cm)

where
f = frequency (MHz) and
a = thickness of specimen (cm).

Here, it should be noted that $\Delta \alpha_r$ varies with the level of surface finish. The one used here is based on the plane surface finished by a surface grinder.

True attenuation constant $\alpha = $ actual $\alpha - \Delta \alpha_d - \Delta \alpha_r$ Although essentially any frequency may be used, limits are set on actual frequency so that the attenuation constant α does not fall below approximately 0.5 dB/cm since the correction term might become large enough to unfavorably affect the accuracy of measurement. When echo cannot be observed because of too heavy attenuation, frequency is lowered to a level where measurement can be achieved.

Figure 5:
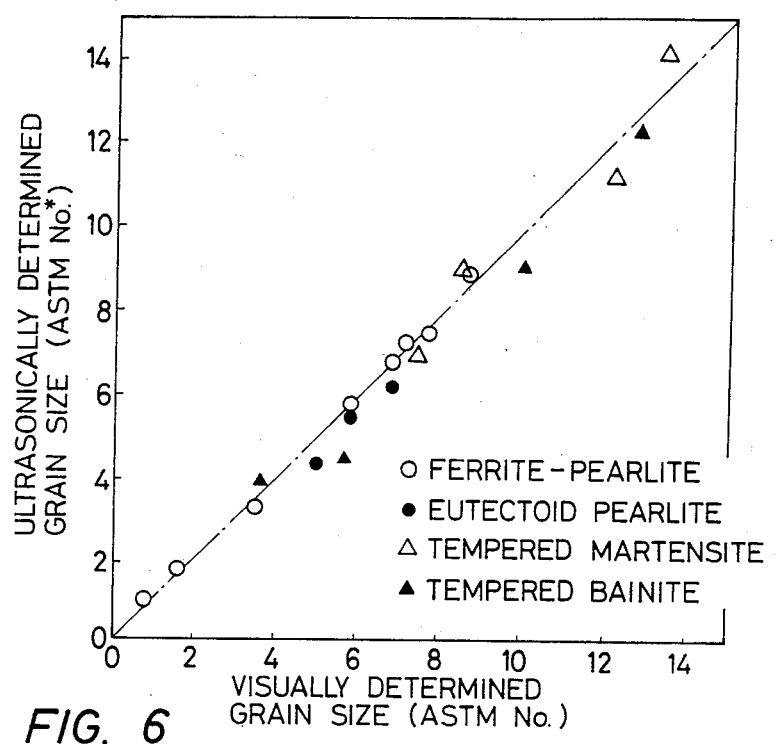
FIG. 5 is a graphical representation of the effective grain size of various structures determined by the method of this invention.

FIG. 5 shows the effective grain sizes of steels of various structures determined by the method of this invention. Translated from the determined grain diameter D, the grain-size No. (hereinafter called ASTM No.*) is in good agreement with the conventional visually determined grain size (ASTM No.). The above translation is carried out according to the following equation.

ASTM No.* = −6.64 log D − 2.06

Figure 6:
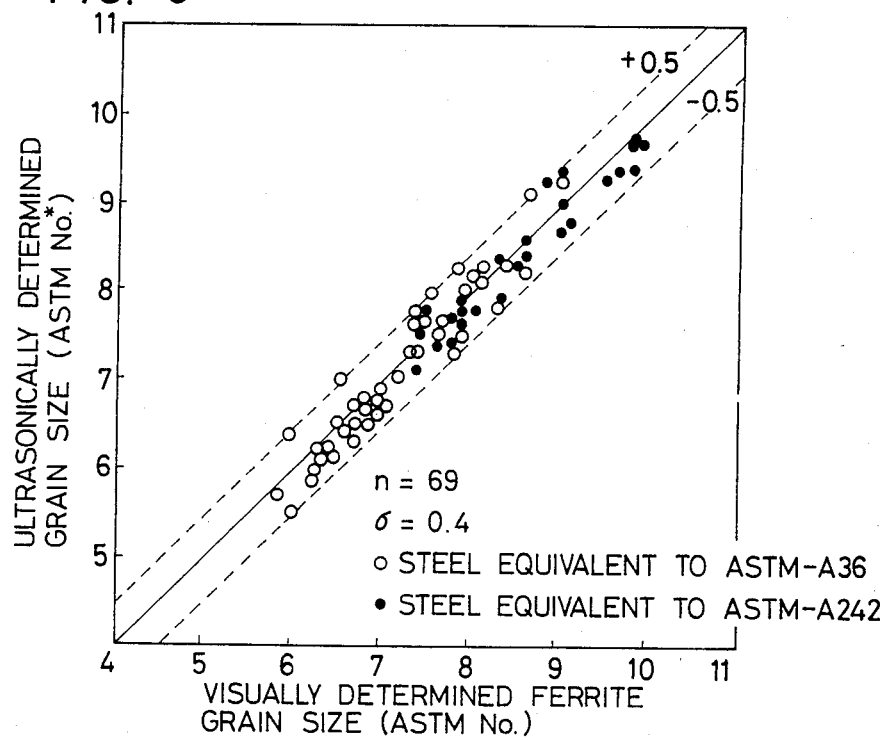
FIG. 6 is a graphical representation of the effective grain size of plate steels determined by the method of this invention.

FIG. 6 shows the grain sizes of commercial steel plates equivalent to ASTM-A 36 and A 242 that were determined by the method of this invention. The plates are 10 mm to 40 mm in thickness and of ferrite-pearlite steel. Where the pearlite content is not higher than 20 percent as with the steels shown in FIG. 6, good agreement is obtained with the ferrite grain size visually determined by the conventional method.

As has been discussed, clear definition of grain diameter was first established based on the concept of effective grains. Then, new equation for determining the grain diameter using the attenuation constant α was formulated. All this has made it possible to determine, using the attenuation of ultrasonic waves, the grain diameter of steel rapidly, accurately and over a wide range of attenuation constants and plate thicknesses.

That is, the grain size can be determined with the attenuation constant of not lower than 0.5 dB/cm, plate thickness of 150 mm and under, and accuracy of ±0.5 ASTM No.

Closely related to the mechanical properties of steel, the effective grain size determined by the method of this invention offers powerful means for the analysis and inspection of steel properties.

Figure 7:
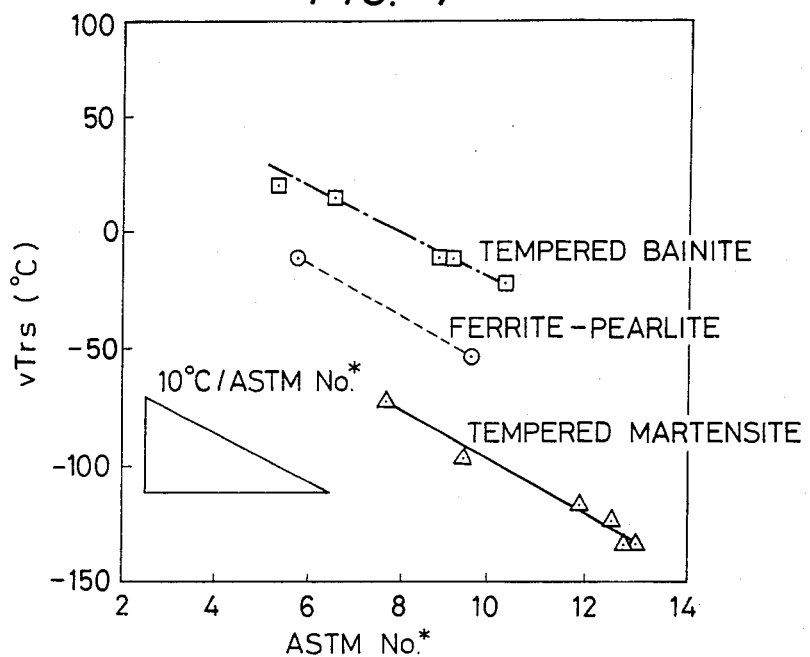
FIG. 7 is a graphical representation of the relationship between the effective grain size of steels determined by the method of this invention and the Charpy transition temperature.

For instance, FIG. 7 graphically shows the relationships between the effective grain size (ASTM No.*) of steels determined by the method of this invention and their transition temperatures. The diagram shows the linear relationships between the effective grain size and transition temperature for steels of different types.

Figure 8:
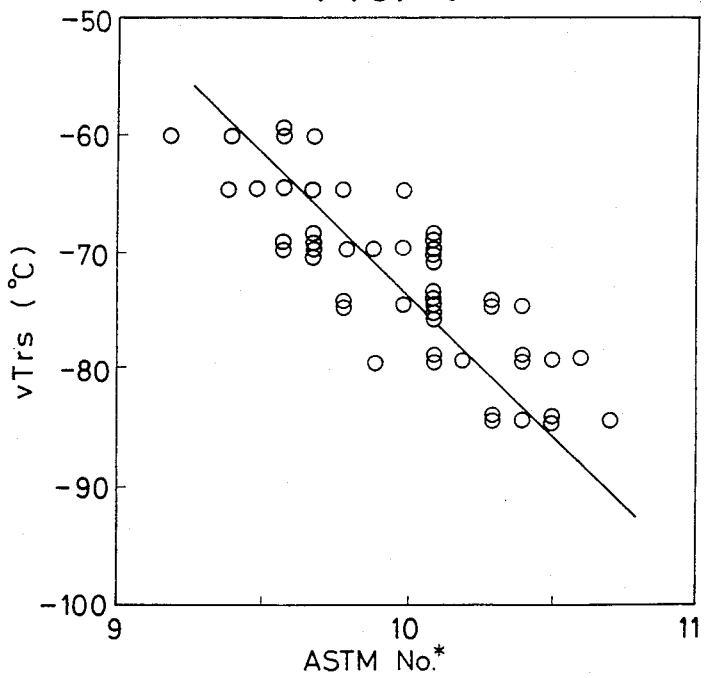
FIG. 8 is a graphical representation of the relationship between the effective grain size of line pipe steels determined by the method of this invention and the Charpy transition temperature.

FIG. 8 shows that line pipe steel (equivalent to API-X-65) exhibits a substantially linear relationship between the effective grain size (ASTM No.*) determined by the method of this invention and the transition temperature. It is known that such mechanical properties of steel as strength and ductility are closely related to the effective grain size.

Figure 9:
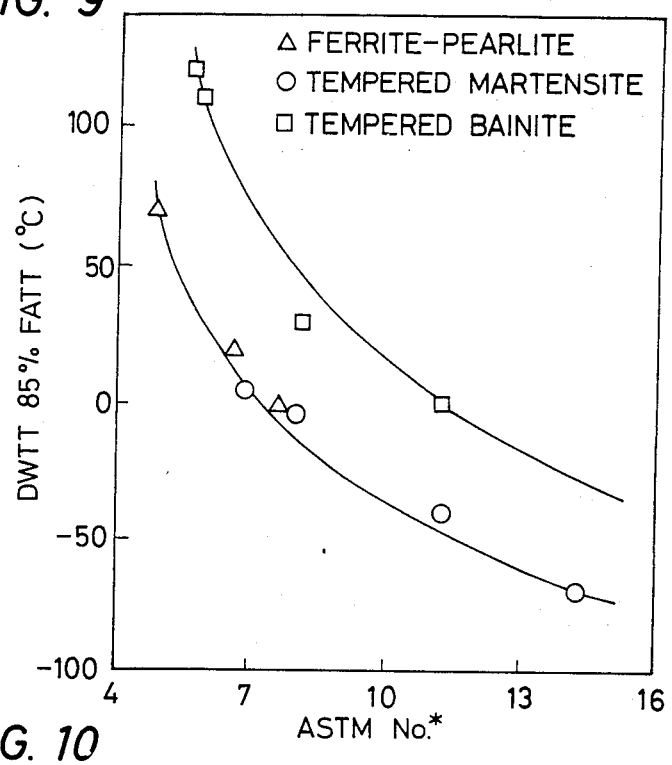
FIG. 9 is graphical representation of the relationship between the effective grain size of steels determined by the method of this invention and the DWTT transition temperature.

FIG. 9 shows the relationships between the effective grain size (ASTM No.*) of different steels determined by the method of this invention and the DWTT transition temperature. The steels tested were vacuum-melted steels conforming to ASTM A533.

Figure 10:
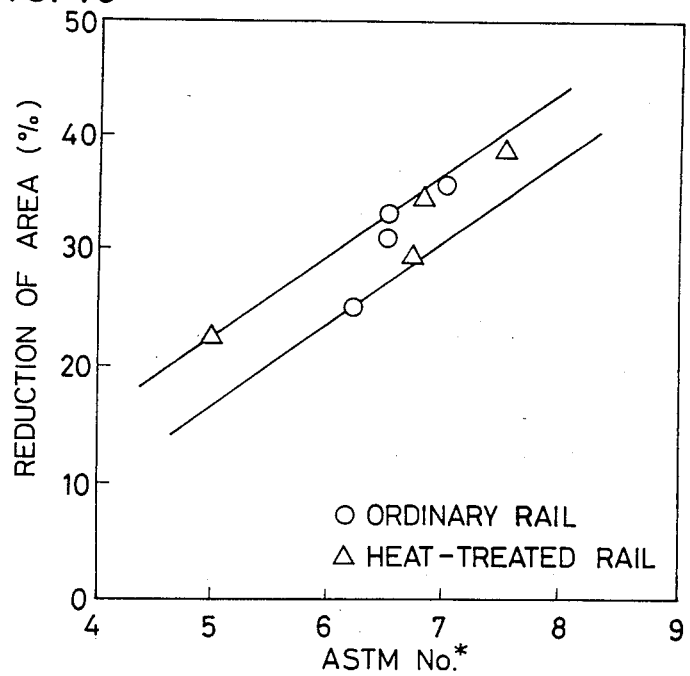
FIG. 10 is a graphical representation of the relationship between the effective grain size of rail steels determined by the method of this invention and the reduction of area.

FIG. 10 shows the relationships between the effective grain size (ASTM No.*) of rail steels determined by the method of this invention and the reduction of area.

The basic principle of this invention described herein can readily be used for the construction of a more sophisticated automatic grain-size determining apparatus that performs the measurement of specimen thickness, setting of ultrasonic wave frequency and grain-size determination automatically by use of microcomputer control or other means.

If the contact-type ultrasonic generator is replaced with a non-contact one, perfectly non-contact grain-size determination is possible.

Although the embodiment described herein relates to the determination of steel grain size, the method of this invention can also be used with such materials as aluminum, titanium and other metals and even with such nonmetallic materials as ceramics.

What is claimed is:

1. A method of determining grain size using ultrasonic waves which comprises propagating ultrasonic waves having a frequency f through an object to be examined, determining the attenuation constant $\alpha$ of the ultrasonic waves, determining the order of the region j to which the value of $f/\alpha$ belongs using the ratio $f/\alpha$ and equation $$C'_j \leq f/\alpha \leq C'_{j+1}$$

where $C'_j$ and $C'_{j+1}$ are constants and j is a constant between 1 and 4, and deriving the grain diameter D from equation $$D = \left(\frac{\alpha}{A_j \cdot f^{n_j+1}}\right)^{\frac{1}{n_j}}$$

using an integer $n_j$ and constant $A_j$ predetermined for the order j of each region.

* * * * *